United States Patent [19]
Thompson

[11] Patent Number: 5,895,980
[45] Date of Patent: Apr. 20, 1999

[54] SHIELDED PACEMAKER ENCLOSURE

[75] Inventor: Thomas T. Thompson, Blaine, Minn.

[73] Assignee: Medical Pacing Concepts, Ltd., Wayzata, Minn.

[21] Appl. No.: 08/775,384

[22] Filed: Dec. 30, 1996

[51] Int. Cl.[6] .................................................. A61N 1/375
[52] U.S. Cl. ........................................................ 607/36
[58] Field of Search ............................. 607/36, 67, 10, 607/63, 2

[56] References Cited

U.S. PATENT DOCUMENTS

| | | | |
|---|---|---|---|
| 3,718,142 | 2/1973 | Mulier | 128/419 P |
| 3,822,707 | 7/1974 | Adducci et al. | 128/419 P |
| 3,842,842 | 10/1974 | Kenny et al. | 607/36 |
| 3,867,950 | 2/1975 | Fischell | 128/419 P |
| 4,152,540 | 5/1979 | Duncan et al. | 607/37 |
| 4,616,655 | 10/1986 | Weinberg et al. | 607/2 |
| 5,314,452 | 5/1994 | Hirschberg et al. | 607/36 |
| 5,470,345 | 11/1995 | Hassler et al. | 607/36 |
| 5,620,476 | 4/1997 | Truex et al. | 607/36 |

FOREIGN PATENT DOCUMENTS

| | | | |
|---|---|---|---|
| 0 331 959 | 9/1989 | European Pat. Off. | 607/36 |
| 0142844 | 7/1980 | Germany | 607/36 |

Primary Examiner—William E. Kamm
Assistant Examiner—Kennedy J. Schaetzle
Attorney, Agent, or Firm—Westman, Champlin & Kelly, P.A.

[57] ABSTRACT

A shielded pacemaker enclosure includes a first portion, and a second portion. Both portions have conductive surfaces disposed thereon. The portions are joined together to form a chamber therein. A connector is provided which extends through the enclosure to receive a lead. Additionally, filter and isolation circuitry is employed to provide further shielding.

21 Claims, 5 Drawing Sheets

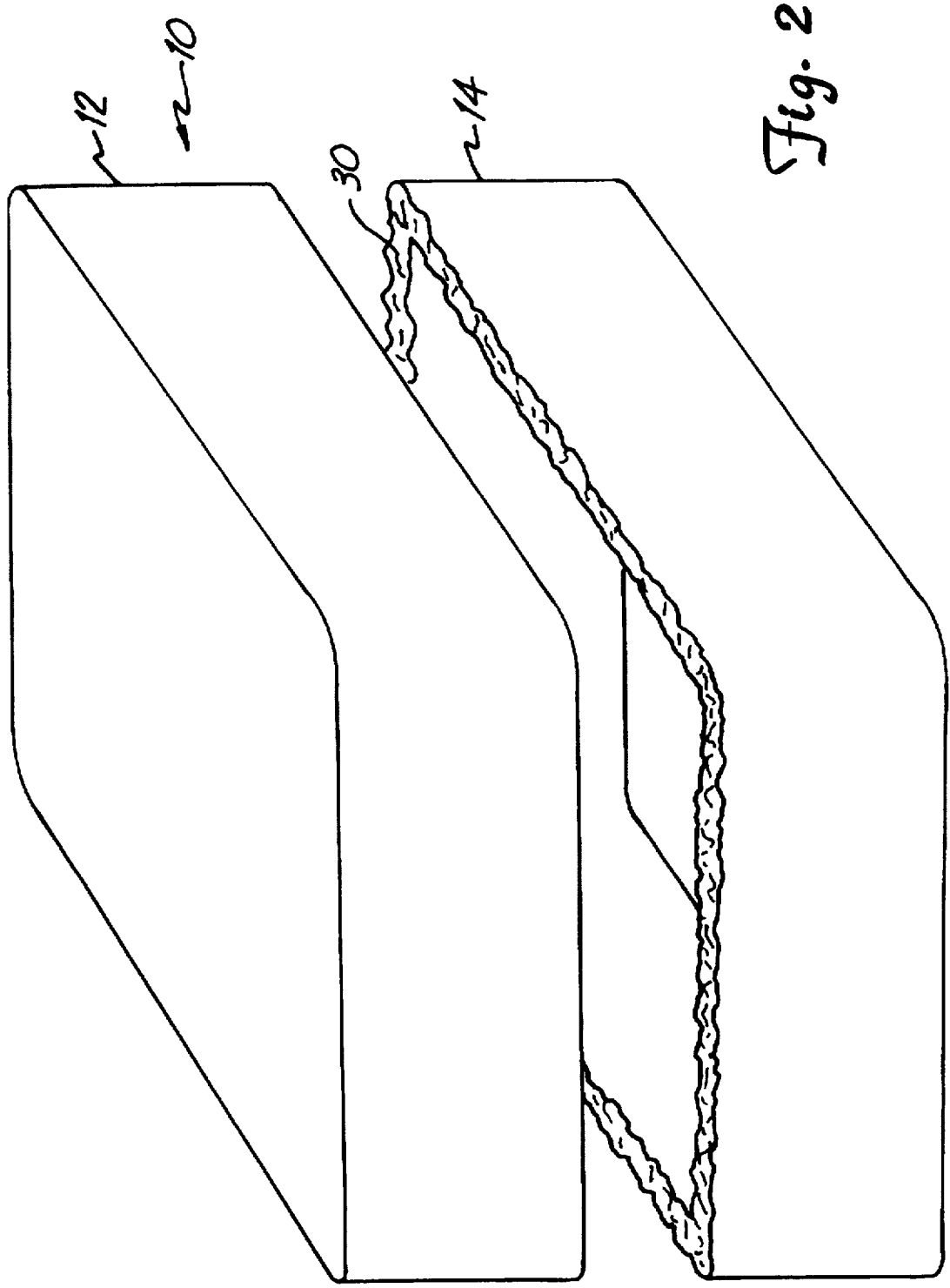

SHIELDED PACEMAKER ENCLOSURE

BACKGROUND OF THE INVENTION

The present invention relates to cardiac pacemakers. More particularly, the present invention relates to a shielded cardiac pacemaker enclosure.

In a normal heart, an electrical stimulus is generated within the right atrium and is transmitted to the ventricle where it produces a contracting or beating of the ventricle. However, heart disease can obstruct the normal conduction of the electrical stimulus within the heart and cause the heart to stop beating at its normal rate. Such a condition results in an array of maladies ranging from fatigue to death.

Cardiac pacemakers have largely alleviated this problem by monitoring the electrical activity of the heart itself and detecting conditions in which the electrical stimulus of the heart is inhibited. When such a condition is detected, the cardiac pacemaker takes over and stimulates the heart in a relatively normal manner until the electrical stimulus regains effective conduction.

In order to sense the minute electrical signals of the heart, the cardiac pacemaker must employ sophisticated, sensitive circuitry. As a result, such circuitry is susceptible to radio frequency interference.

Additionally, radio frequency signals are a ubiquitous part of everyday life. Such signals are generated from overhead power lines, fluorescent lights, microwave ovens, and cellular telephones, to name but a few. Although the human body is able to shield an implantable pacemaker from some forms of radio frequency signals, all pacemakers (both implantable and external) to some degree may be affected by such signals. Thus, a pacemaker may be caused to falsely sense the condition of the heart resulting in inappropriate pacemaker action.

SUMMARY OF THE INVENTION

A shielded pacemaker enclosure includes a first portion, and a second portion. Both portions have a conductive surface disposed thereon. The portions are joined together to form a chamber therein. A connector is provided which extends through the enclosure to receive a lead. Additionally, filter and isolation circuitry is employed in the preferred embodiments to provide further shielding.

BRIEF DESCRIPTION OF THE DRAWINGS

FIG. 2 is a perspective view of a shielded pacemaker enclosure in accordance with the present invention with conductive adhesive interposed between two halves of the enclosure.

DETAILED DESCRIPTION OF THE PREFERRED EMBODIMENTS

Figure 1:
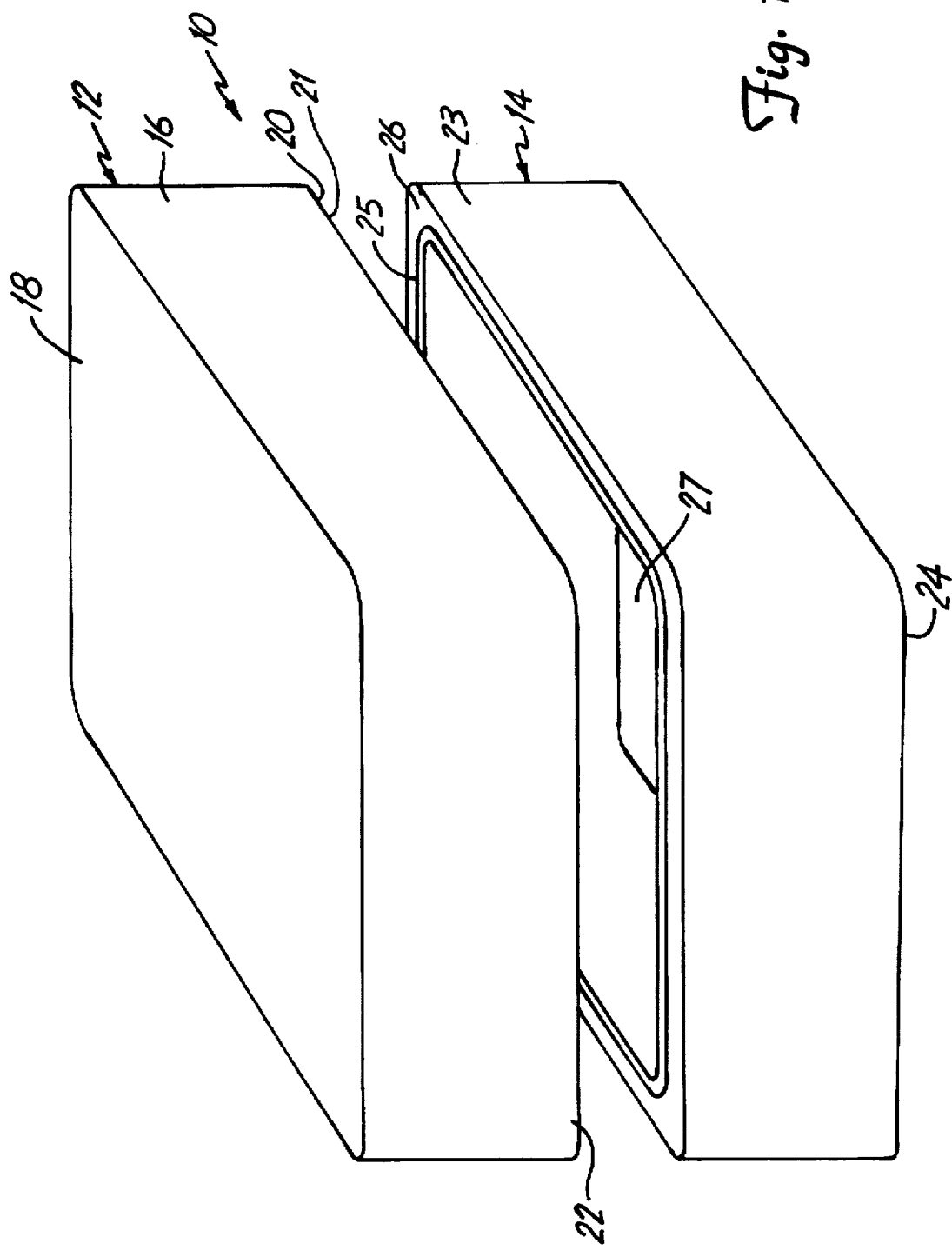
FIG. 1 is a perspective view of a shielded pacemaker enclosure in accordance with the present invention.

FIG. 1 is a partially exploded, perspective view of shielded pacemaker enclosure 10. Enclosure 10 includes top half 12 and bottom half 14. Top half 12 is constructed from a non-conductive material, preferably plastic, and includes a generally rectangular sidewall 16, top 18, conductive upper surface 32 (not shown in FIG. 1), and mating surface 21 (also not shown in FIG. 1). Top half 12 is most preferably constructed from acrylonitrile butadiene styrene (ABS). Sidewall 16 preferably forms a moisture proof seal with top 18 such that upper cavity 22 is formed therein. Bottom half 14 is constructed from a non-conductive material, preferably plastic, and most preferably of the same material as top half 12, and includes substantially rectangular sidewall 23, bottom 24, conductive lower surface 25, and second mating surface 26. Sidewall 23 preferably forms a moisture proof seal with bottom 24 such that a bottom cavity 27 is formed therein. Although halves 12 and 14 are shown to be preferably substantially rectangular, they may take any reasonable shape.

The conductive upper surface 32 is disposed within upper cavity 22, adjacent sidewall 16 and top 18. Conductive upper surface 32 is preferably substantially continuous, and constructed from a metal, most preferably nickel. Lower conductive surface 25 is disposed within bottom cavity 27, adjacent sidewall 23 and bottom 24. Lower conductive surface 25 is also preferably substantially continuous and constructed from a metal, most preferably nickel.

FIG. 2 is a perspective view of shielded pacemaker enclosure 10 in accordance with the present invention. Mating surfaces 21 and 26 preferably mate using a tongue-in-groove or similar configuration which registers the top and bottom portions relative to one another. Conductive adhesive 30 is disposed on mating surface 26 such that when upper half 12 is brought into contact with bottom half 14, conductive adhesive 30 forms a continuous moisture proof seal between, and adheres, top half 12 to bottom half 14, while providing an electrically conductive path between conductive upper surface 32 and conductive lower surface 25. Although using a conductive adhesive is preferred, it is not the only means by which the halves may be joined to practice the invention. For example, an electrical conductor could couple the halves prior to, or after, assembly.

Figure 3:
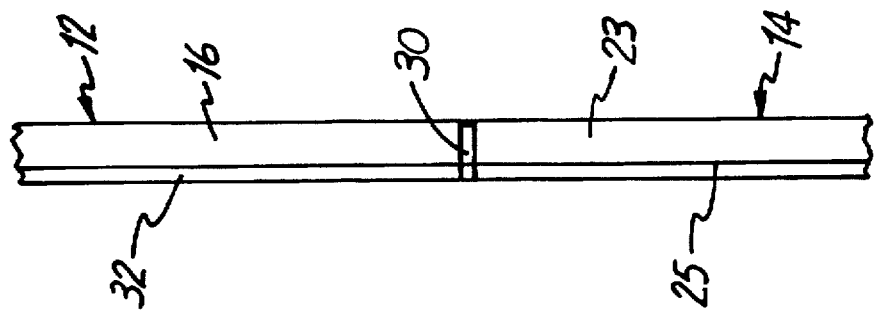
FIG. 3 is a perspective cutaway view of electronic shielding components in accordance with the present invention.

FIG. 3 is an enlarged cut-away elevation view of portions of top half 12 and bottom half 14 in contact with one another via conductive adhesive 30. FIG. 3 shows that conductive adhesive 30 not only provides a structural bond between sidewall 16 and sidewall 23, but also provides an electrical conduction path between upper conductive surface 32 and lower conductive surface 25.

Figure 4:
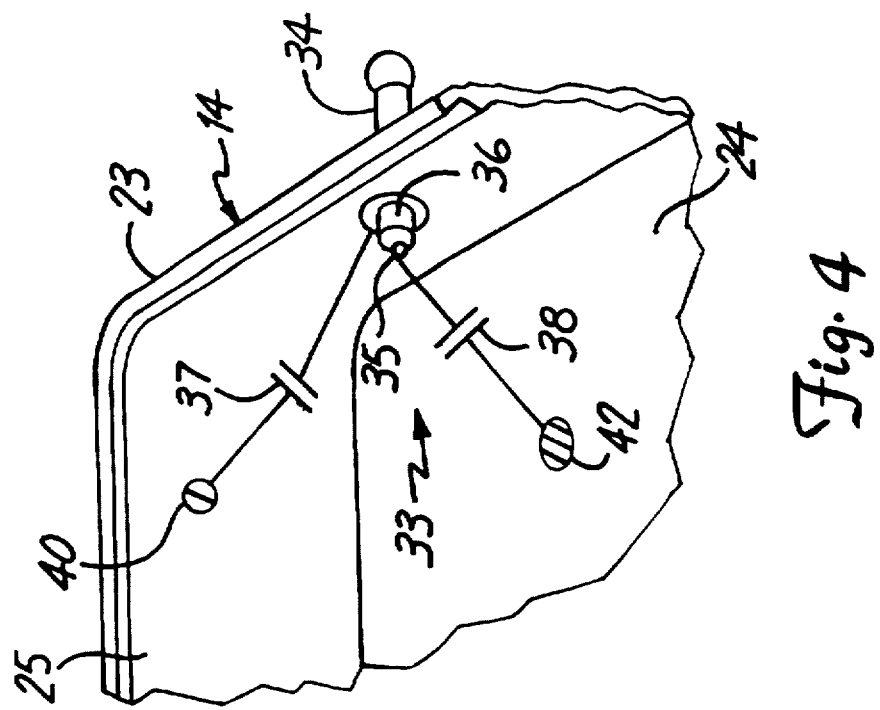
FIG. 4 is a perspective cut-away view of the bottom half in accordance with the present invention.

FIG. 4 shows a perspective cut-away view of bottom half 14 with shielding circuitry 33 in accordance with the present invention. Shielding circuitry 33 preferably includes conductors 35 and 36, capacitors 37 and 38 and pads 40 and 42.

Connector 34 extends through lower sidewall 23 and is fixedly attached thereto. Connector 34 is adapted to receive a lead, preferably a pacing lead which couples the pacemaker to a heart. Connector 34 includes a first conductor 35, and second conductor 36. Capacitors 37 and 38 are each coupled to conductors 35 and 36, and pads 40 and 42, respectively. Pads 40 and 42 are preferably constructed from a conductive material. Pad 40 is attached to lower conductive layer 25 proximate sidewall 23. Also, pad 42 is preferably attached to lower conductive layer 25 proximate bottom 24. Thus, conductors 35 and 36 are capacitively coupled to lower conductive layer 25. Connector 34 is preferably of a phonojack type design, which provides for the coupling of two conductors to a mating connector (not shown). Thus, capacitors 37 and 38 are configured to receive RF signals on the conductors 35 and 36 and effectively shunt such RF interference to lower conductive layer 25.

Figure 5:
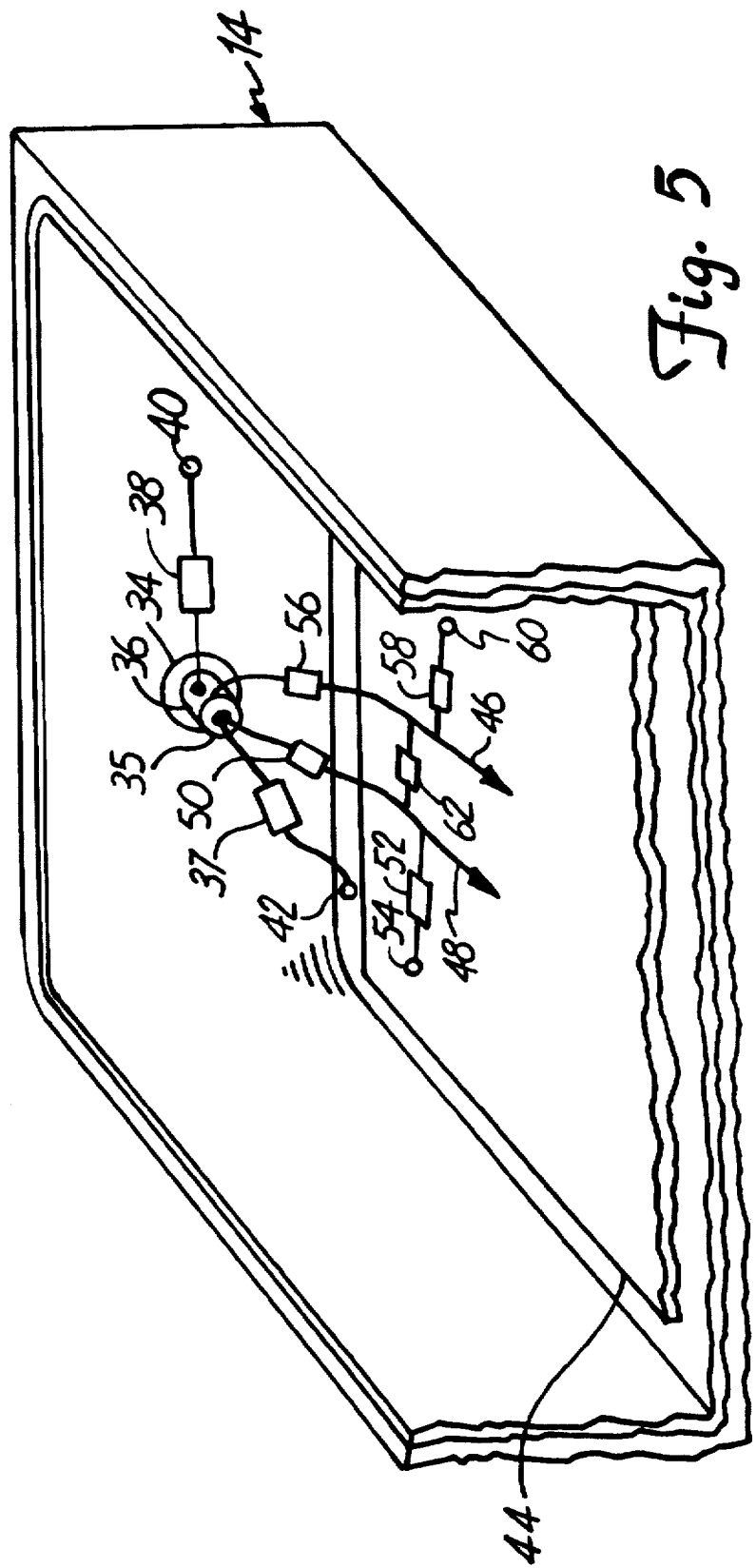
FIG. 5 is a perspective cut-away view of a portion of a pacemaker in accordance with the present invention.

FIG. 5 is a cut-away perspective view of a pacemaker in accordance with the present invention. FIG. 5 includes circuitry 33 shown in FIG. 4 and also includes additional conductors 46 and 48, ferrite beads 50 and 56, Zener regulators 52 and 58 and capacitor 62. Lower half 14 contains circuit board 44 which is preferably attached to bottom surface 27. Circuit board 44 is preferably of printed circuit type design and serves to provide a mount for various circuitry.

FIG. 5 shows that pacemaker output connector 34 is coupled to two additional conductors 46 and 48 which provide positive and negative pacemaker signal outputs, respectively. Conductors 46 and 48 are coupled to a signal amplifier (not shown) which provides an electrical signal which causes the heart to beat. Conductors 46 and 48 are coupled to isolation and filter circuitry in addition to capacitors 36 and 38, described earlier with respect to FIG. 4. First conductor 35 of connector 34, which is coupled to capacitor 37, is also coupled to ferrite bead 50. Ferrite bead 50 is coupled to conductor 48 which is coupled to zener regulator 52. Zener regulator 52 is then coupled to ground 54 of circuit board 44. Second conductor 36 of connector 34 is coupled to ferrite bead 56 which is coupled to conductor 46. Conductor 46 is coupled to Zener regulator 58 which is, in turn, coupled to ground 60 of circuit board 44. Conductors 46 and 48 are coupled together by capacitor 62.

Figure 6:
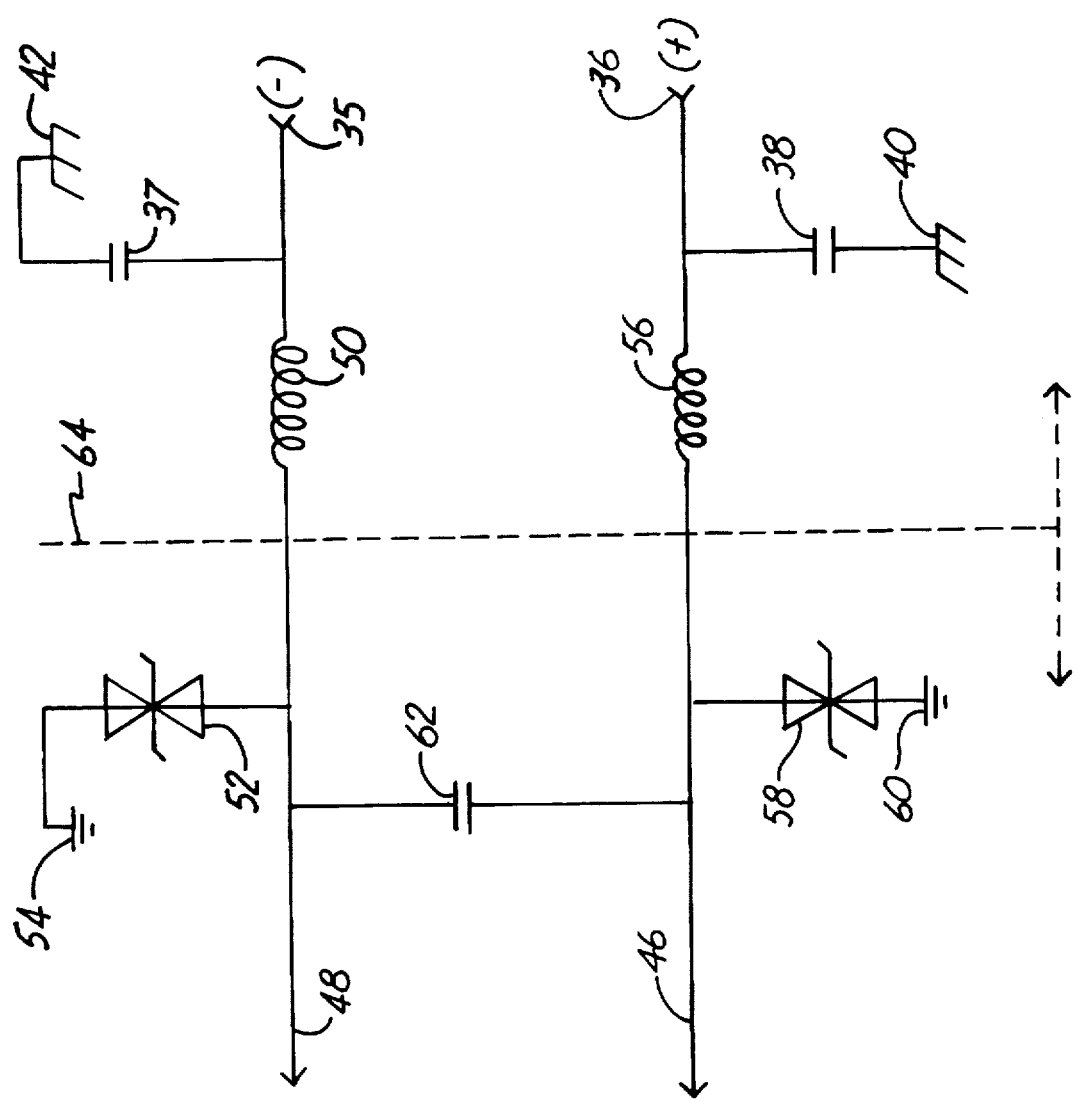
FIG. 6 is a schematic view of filter/isolation circuitry in accordance with the present invention.

FIG. 6 is a schematic view of the filter/isolation circuitry in accordance with the present invention as shown in FIG. 5. The description of the circuit will continue with respect to FIG. 6 for the sake of clarity. First conductor 35 is coupled to capacitor 37 and ferrite bead 50 which is coupled to conductor 48. Capacitor 37 is coupled to conductive layer 25 of casing 42. Similarly, second conductor 36 of connector 34 is coupled to capacitor 38 and ferrite bead 56 which is coupled to conductor 46. Capacitor 38 is coupled to lower conductive layer 25 of lower case 14 by means of conductive bead 40. Thus it can be appreciated that by selecting the characteristics of capacitors 36 and 38 and the inductive characteristics of ferrite beads 50 and 56, heart pacing signals can be passed along conductors 46 and 48 while RF interference is harmlessly shunted to the conductive surface.

In addition, the ground of circuit board 44 is effectively isolated from conductive surfaces 25, 32 of enclosure 10 by means of additional isolation circuitry. Specifically, conductor 48 is coupled to Zener regulator 52 which is preferably of a back-to-back type design, and is coupled to ground 54 of circuit 44. Thus, if a potential residing on conductor 48 exceeds certain parameters determined by the selection of Zener breakdown characteristics of Zener regulator 52, Zener regulator 52 breaks down and allows energy to be passed from conductor 48 to ground 54.

Conductor 46 is coupled to similar circuitry. Conductor 46 is coupled to Zener regulator 58 which is also preferably of a back-to-back type design. Zener regulator 58 is coupled to ground 60 of circuit board 44. Thus, as with conductor 48, if a potential residing on conductor 46 exceeds certain parameters determined by the selection of the Zener breakdown characteristics of Zener regulator 58, then energy from conductor 46 is diverted to ground 60.

Finally, conductor 46 is capacitively coupled to conductor 48 by capacitor 62 to allow for more additional filtering. Specifically, if RF interference induces a potential high enough to breakdown either Zener regulator 52 or Zener regulator 58, and the frequency of the RF interference is high enough to effectively pass through capacitor 62, then both regulators 52 and 58 act to divert the energy into ground connections 54 and 60 of circuit board 44. This effectively provides additional high frequency filtering to the circuit.

Ferrite beads 50 and 56 act as isolators to isolate the circuitry shown in FIG. 6 on the left of dashed line 64 from that shown on the right with respect to RF interference. Those skilled in the art will appreciate that by selecting the proper inductance characteristics of ferrite beads 50 and 56, RF interference will meet with substantial resistance when entering through connector 34, while simultaneously finding an easy path through conductors 36 and 35 to case grounds 40 and 42, respectively. However, the proper selection of ferrite beads 50 and 56 also ensures that cardiac pacing signals passing on conductors 46 and 48 will meet with negligible resistance because such signals are of a much lower frequency than that of RF interference.

Thus, a shielded pacemaker enclosure is provided which shunts radio frequency interference to a conduction shield, while isolating the pacing circuitry from the shield. Therefore, whether the invention is embodied in an external pacemaker or an internal pacemaker, the circuitry of the pacemaker will be shielded from such interference. The present invention may find particular utility with external pacemakers which are subject to more RF interference than are internal pacemakers.

Also, it should also be noted that, while the present description has proceeded with respect to a two electrode system (and is thus suitable to be used as a single chamber internal device) it could also be implemented as a dual chamber internal device. In that case, both pacing and sensing components would be associated with the atrial and ventricular chambers. The device would typically include four electrodes (or both chambers could have a common ground electrode) and an internal switching arrangement. Of course, as noted, the present invention may find particular utility with external pacemakers.

Although the present invention has been described with reference to preferred embodiments, workers skilled in the art will recognize that changes may be made in form and detail without departing from the spirit and scope of the invention.

What is claimed is:

1. A cardiac pacemaker, comprising:
    an enclosure constructed from a non-conductive material the enclosure including first and second portions joined together to form a chamber therein;
    a conductive surface defining an interior of the chamber, disposed adjacent the first and second portions;
    a pacing connector including a first conductor and a second conductor, the pacing connector sealably extending from within the chamber, through the enclosure, the connector adapted to sealably receive a lead;
    filter circuitry disposed within the chamber, including a first capacitor coupling the first conductor to the conductive surface, and a second capacitor coupling the second conductor to the conductive surface; and
    a pacing circuit, having a reference potential connector connected thereto, disposed within the chamber and coupled to the pacing connector such that the reference potential connector is isolated from the conductive surface.

2. The pacemaker of claim 1 further comprising a first inductive member electrically interposed between the first conductor and the pacing circuit, and a second inductive member electrically interposed between the second conductor and the pacing circuit.

3. The pacemaker of claim 2 wherein the first and second inductive members comprise first and second ferrite beads, respectively.

4. The pacemaker of claim 2 further comprising:
a circuit board adapted to support the pacing circuit;
a circuit board reference potential connector coupled to the circuit board;
a first voltage regulator coupled to the first conductor of the pacing connector, and the circuit board reference potential connector; and
a second voltage regulator coupled to the second conductor of the pacing connector, and the circuit board reference potential connector.

5. The pacemaker of claim 4 further comprising a capacitor coupled to the first conductor of the pacing connector and the second conductor of the pacing connector.

6. The pacemaker of claim 1 wherein the conductive surface is substantially continuous.

7. The pacemaker of claim 1 wherein the conductive surface is constructed from nickel.

8. The pacemaker of claim 1 wherein the first capacitor of the filter circuitry, and second capacitor of the filter circuitry are attached electrically and mechanically to the conductive surface by means of a conductive adhesive.

9. The pacemaker of claim 1 wherein the first and second portions are constructed from plastic suitable for implantation into a human body.

10. A shielded pacemaker enclosure comprising:
a first portion including a first recess;
a first conductive surface disposed within the first recess;
a second portion including a second recess;
a second conductive surface disposed within the second recess;
a conductive adhesive layer electrically coupling the first and second conductive surfaces; and
a connector including a first conductor and a second conductor, the connector extending through said first and second portions.

11. The enclosure of claim 10 further comprising:
a first capacitor coupled to the first conductor, and one of the first conductive surface and second conductive surface; and
a second capacitor coupled to the second conductor and one of the first conductive surface and second conductive surface.

12. The enclosure of claim 10 further comprising:
a circuit board having a ground, and adapted to mount pacing circuitry;
a first voltage regulator including a first pair of Zener diodes arranged in back-to-back fashion, coupling the first conductor to the circuit board ground; and
a second voltage regulator including a second pair of Zener diodes arranged in back-to-back fashion, coupling the second conductor to the circuit board ground.

13. The enclosure of claim 10 wherein the first conductive surface is substantially continuous, and the second conductive surface is substantially continuous.

14. The enclosure of claim 10 wherein the first conductive surface and the second conductive surface are constructed from nickel.

15. The enclosure of claim 10 wherein the first portion and the second portion are constructed from plastic.

16. The enclosure of claim 15 wherein the first portion and the second portion are constructed from acrylonitrile butadiene styrene (ABS).

17. An external pacemaker comprising:
an enclosure including a first external part defining a first recess with a first conductive surface disposed therein, and a second external part with a second conductive surface disposed on a portion thereof, and a conductive layer joining the first and second conductive surfaces such that a chamber is formed therein, and the conductive surfaces are electrically coupled;
a pacing connector including a first conductor and a second conductor, the pacing connector extending from within the chamber through the enclosure, and adapted to receive a lead;
a pacing circuit disposed within the chamber and coupled to the pacing connector; and
a power source providing power to the pacing circuitry.

18. The pacemaker of claim 17 further comprising:
a first capacitor coupled to the first conductor, and one of the first conductive surface and second conductive surface; and
a second capacitor coupled to the second conductor and one of the first conductive surface and second conductive surface.

19. The pacemaker of claim 17 wherein the first conductive surface is substantially continuous, and the second conductive surface is substantially continuous.

20. The pacemaker of claim 17 wherein the first and second conductive surfaces are constructed from nickel.

21. The pacemaker of claim 17 wherein the first and second external parts are constructed from plastic.

* * * * *